United States Patent [19]
Halm et al.

[11] 4,402,797
[45] Sep. 6, 1983

[54] SEPARATION OF CHLOROSILANES BY EXTRACTIVE DISTILLATION

[75] Inventors: Roland L. Halm, Madison, Ind.; Stefan F. Rentsch, Carrollton, Ky.

[73] Assignee: Dow Corning Corporation, Midland, Mich.

[21] Appl. No.: 419,856

[22] Filed: Sep. 20, 1982

[51] Int. Cl.³ .............................. B01D 3/40; C07F 7/20
[52] U.S. Cl. .......................................... 203/58; 203/52; 203/68; 203/70; 203/84; 556/466; 556/472
[58] Field of Search ...................... 203/58, 57, 71, 84, 203/68–70, 52; 556/466, 472, 465

[56] References Cited

U.S. PATENT DOCUMENTS

| | | | |
|---|---|---|---|
| 2,388,575 | 11/1945 | Sauer et al. | 556/466 X |
| 3,007,956 | 11/1961 | Linville et al. | 556/466 |
| 3,114,678 | 12/1963 | Megantz et al. | 556/466 X |
| 3,352,765 | 11/1967 | Warner et al. | 203/70 |
| 4,021,490 | 5/1977 | Hudson | 203/58 X |
| 4,024,028 | 5/1977 | Haskell | 203/58 X |

FOREIGN PATENT DOCUMENTS 709630  1/1980  U.S.S.R. ............................ 556/466

OTHER PUBLICATIONS

Sivtsova et al., J. Appl. Chem USSR, 38, 2549 (1966).
Sivtsova et al., J. Appl. Chem USSR, 39, 1908 (1967).
Sivtsova et al., J. Appl. Chem USSR, 41,447 (1969).
Russian Patent 165,445 appearing in *Soviets Inventions Illustrated*, Jun., 1965.
Russian Patent 275,054 appearing in *Soviets Inventions Illustrated*, Mar., 1971.

*Primary Examiner*—Wilbur L. Bascomb, Jr.
*Attorney, Agent, or Firm*—Richard A. Kaba

[57] ABSTRACT

An improved method for the separation of close-boiling chlorosilanes is described. The method consists of the extractive distillation of the close-boiling chlorosilanes using sulfolane as the extractive solvent and thereafter separating the higher-boiling chlorosilane and sulfolane by distilling the higher-boiling chlorosilane from the higher-boiling chlorosilane and sulfolane mixture to which is added a hydrocarbon solvent. Preferred hydrocarbon solvents include normal-heptane, normal-nonane, and 2,2,4-trimethylpentane. The sulfolane obtained from the higher-boiling chlorosilane and sulfolane mixture is suitable for recycling to the extractive distillation process as the sulfolane contains only limited amounts of dissolved chlorosilane.

10 Claims, No Drawings

SEPARATION OF CHLOROSILANES BY EXTRACTIVE DISTILLATION

BACKGROUND OF THE INVENTION

During the reaction of methyl chloride with silicon a mixture of chlorosilanes is produced. These chlorosilanes are normally separated by fractional distillation. Two of the largest volume chlorosilanes produced by this method are methyltrichlorosilane and dimethyldichlorosilane. In order to prepare satisfactory siloxane polymers from dimethyldichlorosilane it is usually necessary that the methyltrichlorosilane content of dimethyldichlorosilane be less than about 500 parts per million. The boiling points of these materials are sufficiently close that distillation columns of 200 or more stages are required to satisfactorily separate these materials in commercial operation. Consequently at the present time a large capital investment is required in order to install these columns and it would highly desirable to reduce this capital investment. Also, a large column generally requires more energy to operate than does a smaller column.

The copending application Ser. No. 06/419,854 of Ora L. Flaningam and Roland L. Halm, filed on Sept. 20, 1982, the same data and assigned to the same assignee as this present application, discloses a method by which the separation of close-boiling chlorosilanes can be carried out in a more efficient and less costly manner. The method involves the separation of close-boiling chlorosilanes by the procedures of extractive distillation using sulfolane as the extractive solvent where the lower-boiling chlorosilane is distilled from a mixture of the close-boiling chlorosilanes and sulfolane and thereafter separating the higher-boiling chlorosilane and the sulfolane. Sulfolane is tetrahydrothiophene-1,1-dioxide. Flaningam et al. discloses that the higher-boiling chlorosilane can be separated from the mixture of the higher-boiling chlorosilane and sulfolane by such techniques as gas-liquid chromatograph and distillation. Clearly, for a commerical chlorosilane plant, distillation would be the more viable procedure. Flaningam et al. further teaches that in large scale operations it is preferred that sulfolane be employed in amounts greater than 15% by weight with the preferred range being 50-90% by weight based on the total weight of chlorosilanes in the extractive distillation column. Based on the teachings of Flaningam et al. one skilled in the art would realize that in the commercial extractive distillation of chlorosilanes, using the solvent sulfolane, rather large amounts of sulfolane would be required and the process would be most attractive if the sulfolane could be recycled. For the process to be most efficient the recycled sulfolane should be virtually free of the higher-boiling chlorosilane. Otherwise, because in the preferred operation of the Flaningam et al. method the sulfolane is introduced near the top of the extractive distillation column, a significant amount of the higher-boiling chlorosilane in the sulfolane would go overhead with the lower-boiling chlorosilane. In such a situation the overall efficiencies of the process would be reduced. To obtain sulfolane virtually free of higher-boiling chlorosilane by simple distillation, it is required that sulfolane be heated very close to its pure component boiling point (285° C. at atmospheric pressure) in the sulfolane recovery column. Unfortunately, sulfolane begins to undergo thermal decomposition at about 180° C. Above about 220° C. the thermal decomposition of sulfolane becomes especially rapid. Therefore, to minimize the thermal decomposition of sulfolane the temperature in the column used to separate the higher-boiling chlorosilane and sulfolane must be kept under about 180° C. Under these conditions with a condensor pressure of about 1 atmosphere in the separation of dimethyldichlorosilane and methyltrichlorosilane, the recycled sulfolane can contain 3% by weight or more dimethyldichlorosilane. The introduction of such large amounts of dimethyldichlorosilane in the top of the extractive disillation column in the separation of methyltrichlorosilane and dimethyldichlorosilane can lower the overall efficiencies of the process.

One object of this present invention is to provide a method for recovering sulfolane virtually free of the higher-boiling chlorosilane from a mixture of the sulfolane and a higher-boiling chlorosilane obtained from the extractive disillation of close-boiling chlorosilanes without subjecting the sulfolane to prohibitively high temperature.

Another object of this present invention is to provide a method by which sulfolane used in the extractive distillation of close-boiling chlorosilanes can be recovered in a form and purity such the sulfolane can more efficiencly be reused or recycled in the extractive distillation process.

Still another object of this present invention is to provide an improved method for the separation of close-boiling chlorosilanes.

Other objects of the present invention will be apparent to those skilled in the art upon examination of this specification.

SUMMARY OF THE INVENTION

This invention relates to an improved method of separating close-boiling chlorosilanes which comprises the removal of the lower-boiling chlorosilane from a mixture of close-boiling chlorosilanes by extractive distillation using sulfolane as the extractive solvent and thereafter separating the sulfolane and the higher-boiling chlorosilane where the improvement comprises of separating the sulfolane and the higher-boiling chlorosilane by distilling the higher-boiling chlorosilane from a mixture of the sulfolane and the higher-boiling chlorosilane to which has been added a hydrocarbon solvent where the boiling point of the hydrocarbon solvent at atmospheric pressure is between 10° C. above the boiling point of the higher-boiling chlorosilane and 175° C. and where the solubility of the hydrocarbon solvent in sulfolane is less than about 5% by weight at about 30° C. and where the hydrocarbon solvent is added to the mixture of sulfolane and higher-boiling chlorosilane in an amount exceeding the solubility of the hydrocarbon solvent in sulfolane at the operating temperature of the distillation such that two liquid phases are present; and thereafter separating the sulfolane and the hydrocarbon solvent.

The extractive distillation of close-boiling chlorosilanes using sulfolane as the extractive solvent can be carried out by the procedures taught in Flaningam et al. which is hereby incorporated by reference in its entirety. The separation of the close-boiling chlorosilanes can be carried out in any suitable manner such as by mixing the chlorosilanes and sulfolane in a retort and then heating to remove the lower-boiling chlorosilane. Alternatively, the vapors of the mixed chlorosilanes can be passed into the sulfolane which is maintained at a temperature above the boiling point of the lower-boiling chlorosilane. The preferred method of Flaningam et al. is to pass the sulfolane countercurrently to the vapors of the mixed chlorosilanes. On a commercial scale this preferred method can be conveniently carried out in a distillation column or tower where the liquid sulfolane is introduced near the top of the column or tower and then flows down the column or tower and where the chlorosilanes are introduced at a point or points lower in the column or tower. The temperature of the column or tower should be regulated so that the liquid sulfolane flowing down the column comes into contact with vapors of the mixed chlorosilanes rising in the column and with the condensed vapors on the trays in the column below the sulfolane feed tray. After the lower-boiling chlorosilane has been removed, the sulfolane and higher-boiling chlorosilane are separated. The present invention relates to an improved method of separating the sulfolane and the higher-boiling chlorosilane. The present invention also relates to an improved method by which the overall efficiencies of the extractive distillation of close-boiling chlorosilanes using sulfolane as the solvent are improved.

To obtain maximum benefits from the method of Flaningam et al. it is apparent that the sulfolane solvent must be recycled. If the recycled sulfolane contains significant amounts of the higher-boiling chlorosilane then a significant amount of the higher-boiling chlorosilane is returned to be distilled a second time. This repeated distillation of the higher-boiling chlorosilane decreases the efficiency of the system and also the capacity of the distillation column. An additional economic loss results if the recycled sulfolane contains significant amounts of the higher-boiling chlorosilane when the preferred method of extractive distillation as taught by Flaningam et al. is employed since the recycled sulfolane is introduced at or near the top of the distillation column.

The recycled sulfolane can be made virtually free of chlorosilane without exposing the sulfolane to temperatures above 180° C. by distilling the higher-boiling chlorosilane from sulfolane in the presence of a hydrocarbon solvent. The hydrocarbon solvent employed in this invention should have a boiling point at 760 mm Hg in the range of 10° C. above the boiling point of the higher-boiling chlorosilane and 175° C. and preferably between 20° C. above the boiling point of the higher-boiling chlorosilane and 155° C. In other words, the boiling point of the hydrocarbon solvent should be higher than the boiling points of the chlorosilanes to be separated but below the temperature at which sulfolane decomposes. The hydrocarbon solvent useful in this invention should also have only limited solubility in sulfolane. This solubility of the hydrocarbon solvent in sulfolane at 30° C. should be less than about 5% by weight or preferably less than about 2.5 by weight. Additionally, the hydrocarbon solvent should be stable in and nonreactive towards mixtures of chlorosilanes and sulfolane.

The hydrocarbon solvents useful in the present invention include both saturated and unsaturated hydrocarbons. These hydrocarbon solvents can be linear, branched, or cyclic hydrocarbons. Examples of hydrocarbon solvents useful in the present invention include normal alkanes such as heptane, octane and nonane; branched alkanes such as 2,2,4-trimethylpentane, 2-methylheptane, 3-methylheptane, 4-methylheptane, 4-ethylheptane, 2,3-dimethylheptane and 2,4-dimethylheptane; alkenes such as 1-heptene, 2-heptene, 1-octene and 2-octene; and cyclic hydrocarbons such as methylcyclohexane, cycloheptane and methylcycloheptane. The preferred hydrocarbon solvents for the practice of the present invention are normal-heptane, normal-nonane, and 2,2,4-trimethylpentane. 2,2,4-Trimethylpentane is also commercially available under the name isooctane. Blends of various hydrocarbon solvents can also be employed in the present invention. Examples of suitable solvent blends include Isopar C and Isopar E (tradenames) from Exxon Corporation which have boiling point ranges of 97°–107° C., and 116°–134° C., respectively. Solvent blends employed in this invention should have boiling point ranges between 10° C. above the boiling point of the higher-boiling chlorosilane and 175° C. and preferably between 20° C. above the boiling point of the higher-boiling chlorosilane and 155° C. The total solubility of the solvent blend in sulfolane at 30° C. should be less than 5% by weight and preferably less than 2.5% by weight. It is also preferred that the boiling point range of the solvent blend be less than about 20° C.

The amount of the hydrocarbon solvent added to the solfolane/higher-boiling chlorosilane mixture is not critical so long as sufficient hydrocarbon solvent is added to insure a two phase system at the operating temperature of the solvent recovery column where one phase is essentially hydrocarbon free and the other phase is essentially sulfolane free. The higher-boiling chlorosilane is distributed between the two phases. However, it is preferred that the hydrocarbon solvent be added in such amounts that the hydrocarbon solvent to sulfolane ratio be in the range of about 1:12 to about 1:1 by weight.

The present invention can be carried out by mixing the hydrocarbon solvent with the higher-boiling chlorosilane and sulfolane mixture by any appropriate means or method. One such method would be to simply add both the hydrocarbon and the chlorosilane and sulfolane mixture to the reboiler of a distillation column. Another method would be to add either the hydrocarbon or the chlorosilane and sulfolane mixture or both to various locations in a distillation column. The hydrocarbon solvent, chlorosilane, and sulfolane mixture is then heated to selectively remove the chlorosilane. The removal of the chlorosilane is preferably done in a distillation column where the chlorosilane is collected as the overhead product. This distillation can be carried out at atmospheric pressure as well as above and below atmospheric pressure. This distillation can be operated in a batch, semi-continuous, or continuous mode.

After removal of the chlorosilane, the hydrocarbon solvent and the sulfolane can be separated by any suitable manner such as by distillation or phase separation. The preferred method is to phase separate the mixture whereby one phase or layer consists essentially of the hydrocarbon solvent and the other phase or layer consists essentially of sulfolane. The phase separation can be carried out at any suitable temperature between the melting point of the solfolane and the boiling point of the hydrocarbon solvent. The hydrocarbon solvent can be recycled back to the distillation column where the higher-boiling chlorosilane is removed from the sulfolane. The sulfolane can be recycled to the extractive distillation column. The introduction of small amounts of the hydrocarbon solvent present in the recycled sulfolane does not appear to adversely effect the extractive distillation procedure to any great extent.

The preferred close-boiling chlorosilanes mixtures to be separated by the improved method of this present invention are mixtures of methyltrichlorosilane and dimethyldichlorosilane where dimethyldichlorosilane is the higher-boiling chlorosilane and mixtures of dimethyldichlorosilane and ethyldichlorosilane where ethyldichlorosilane is the higher-boiling chlorosilane.

The following examples are illustrative only and shall not be construed as limiting the invention.

EXAMPLE 1

This examples shows the removal of dimethyldichlorosilane from sulfolane using normal-heptane as the hydrocarbon solvent. Normal heptane has a boiling point of about 98° C. at atmospheric pressure. The column used was a 25 stage bubble cap column (1 inch in diameter) with about 10 inches of wire mesh packing between the bubble cap portion and the reboiler. The dimethyldichlorosilane (about 10% by weight) in sulfolane at a temperature of about 27° C. was continuously introduced into the column at the bottom of the bubble cap portion; about 500 ml of normal-heptane was introduced directly into the reboiler. The distillation was carried out in a continuous mode at a condenser pressure of about one atmosphere and a reflux ratio of 10:1. Distillate dimethyldichlorosilane was taken overhead at a rate of about 20-30 cc/hr. Every hour sulfolane was drained from the reboiler so that the volume of material remained approximately constant thereby separating the sulfolane and hydrocarbon solvent. After the column had achieved steady state operation, samples from both the overhead product and the sulfolane from the bottom stream were collected and analyzed using standard gas liquid chromatographic techniques. At the time of analysis, the reboiler contained about 700 ml of sulfolane and 500 ml of normal-heptane. The amount of sulfolane in the distillate dimethyldichlorosilane was below the detection limits.

| Run No. | Temperature (°C.) | | n-heptane in Distillate $Me_2SiCl_2$ | $Me_2SiCl_2$ in Sulfolane bottoms |
|---|---|---|---|---|
| | Overhead | Reboiler | | |
| 1 | 69.3 | 111 | 0.0335% | 0.010% |
| 2 | 69.6 | 101 | 0.039% | 0.778% |

EXAMPLE 2

This example shows the removal of dimethyldichlorosilane from sulfolane using normal-nonane as the hydrocarbon solvent. Normal-nonane has a boilint point of about 151° C. at atmospheric pressure. The same column as described in Example 1 was employed. A dimethyldichlorosilane (about 25% by weight) and sulfolane mixture was used as the feed material. About 600 ml of normal-nonane was added to the reboiler. The procedures employed were as described in Example 1. The results of the analysis are given below. Sulfolane was not detected (ND) in the distillate dimethyldichlorosilane.

| Run No. | Temperature (°C.) | | n-nonane in Distillate $Me_2SiCl_2$ | $Me_2SiCl_2$ in Sulfolane bottoms |
|---|---|---|---|---|
| | Overhead | Reboiler | | |
| 1 | 69.6 | 143 | 0.027% | 1.06% |
| 2 | 69.6 | 155-158 | 0.118% | 0.59% |
| 3 | 69.6 | 155-158 | ND | ND |

COMPARATIVE EXAMPLE

This example demonstrates the distillation of dimethyldichlorosilane from sulfolane without any added hydrocarbon solvent. The distillations were carried out in a batch mode by heating a mixture of about 10-15% by weight dimethyldichlorosilane in sulfolane at a constant reboiler temperature and removing all the overhead product dimethyldichlorosilane that could be distilled from the mixture. The distillation was carried out in a simple distillation apparatus. The sulfolane remaining after removal of the distillate was analyzed for any remaining dimethyldichlorosilane.

| Run No. | Reboiler Temp (°C.) | $Me_2SiCl_2$ in Sulfolane Bottoms |
|---|---|---|
| 1 | 145 | 4.3% |
| 2 | 173 | 3.4% |
| 3 | 180 | 3.2% |

From this comparative example it is easy to see that distillation of chlorosilane from sulfolane without the addition of a hydrocarbon solvent, even at the high temperature of 180° C., results in sulfolane containing significant amounts of the chlorosilane.

That which is claimed is:

1. In a method of separating close-boiling chlorosilanes which comprises the removal of the lower-boiling chlorosilane from a mixture of close-boiling chlorosilanes by extractive distillation using sulfolane as the extractive solvent and thereafter separating the sulfolane and the higher-boiling chlorosilane, the improvement comprising of separating the sulfolane and the higher-boiling chlorosilane by distilling the higher-boiling chlorosilane from a mixture of the sulfolane and the higher-boiling chlorosilane to which has been added a hydrocarbon solvent where the boiling point of the hydrocarbon solvent at atmospheric pressure is between 10° C. above the boiling point of the higher-boiling chlorosilane and 175° C. and where the solubility of the hydrocabon solvent in sulfolane is less than about 5% by weight at about 30° C. and where the hydrocarbon solvent is added to the mixture of sulfolane and higher-boiling chlorosilane in an amount exceeding the solubility of the hydrocarbon solvent in sulfolane at the operating temperature of the distillation such that two liquid phases are present; and thereafter separating the sulfolane and the hydrocarbon solvent.

2. A method as defined in claim 1 wherein the boiling point of the hydrocarbon solvent at atmospheric pressure is between 20° C. higher than the boiling point of the higher-boiling chlorosilane and 155° C. and where the solubility of the hydrocarbon solvent in sulfolane is less than about 2.5% by weight at about 30° C.

3. A method as defined in claim 2 wherein the sulfolane and the hydrocarbon solvent, after removal of the higher-boiling chlorosilane, are separated by collecting separately the two liquid phases where one phase consists essentially of sulfolane and the second phase consists essentially of the hydrocarbon solvent.

4. A method as defined in claims 1, 2, or 3 wherein the lower-boiling chlorosilane is methyltrichlorosilane and the higher-boiling chlorosilane is dimethyldichlorosilane.

5. A method as defined in claims 1, 2, or 3 wherein the lower-boiling chlorosilane is dimethyldichlorosilane and the higher-boiling chlorosilane is ethyldichlorosilane.

6. A method as defined in claims 1, 2, or 3 wherein the hydrocarbon solvent is selected from the group consisting of normal-heptane, normal-nonane, 2,2,4-trimethylpentane, 1-octene, and methylcyclohexane.

7. A method as defined in claim 4 wherein the hydrocarbon solvent is normal-heptane.

8. A method as defined in claim 4 wherein the hydrocarbon solvent is normal-nonane.

9. A method as defined in claim 4 wherein the hydrocarbon solvent is 2,2,4-trimethylpentane.

10. A method as defined in claims 1,2, or 3 wherein the resulting sulfolane obtained by separating the sulfolane and hydrocarbon solvent contains less than 1% by weight of the higher-boiling chlorosilane and where the resulting sulfolane is recycled as the extractive solvent in the extractive distillation.

* * * * *

UNITED STATES PATENT AND TRADEMARK OFFICE
CERTIFICATE OF CORRECTION

PATENT NO. : 4,402,797
DATED : September 6, 1983
INVENTOR(S) : Roland L. Halm and Stefan F. Rentsch It is certified that error appears in the above—identified patent and that said Letters Patent is hereby corrected as shown below:

Column 1, line 26; the line reading "20, 1982, the same data and assigned to the same as-" should read "the same date and assigned to the same as-"

Column 1, line 42; the line reading "commerical chlorosilane plant, distillation would be the" should read "commercial chlorosilane plant, distillation would be the"

Column 5, line 52; the line reading "drocarbon solvent. Normal-nonane has a boilint point of" should read "drocarbon solvent. Normal-nonane has a boiling point of"

Signed and Sealed this

Fifteenth Day of November 1983

[SEAL]

Attest:

GERALD J. MOSSINGHOFF

Attesting Officer

Commissioner of Patents and Trademarks